US00PP31691P3

(12) United States Plant Patent
Dirr et al.

(10) Patent No.: US PP31,691 P3
(45) Date of Patent: Apr. 21, 2020

(54) CRAPEMYRTLE PLANT NAMED 'DJ 01-14'

(50) Latin Name: ***Lagerstroemia* hybrid**
Varietal Denomination: DJ 01-14

(71) Applicant: University of Georgia Research Foundation, Inc., Athens, GA (US)

(72) Inventors: Matthew A. Dirr, Watkinsville, GA (US); Donglin Zhang, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/350,965

(22) Filed: Feb. 5, 2019

(65) Prior Publication Data

US 2019/0246541 P1 Aug. 8, 2019

Related U.S. Application Data

(60) Provisional application No. 62/627,058, filed on Feb. 6, 2018.

(51) Int. Cl.
*A01H 5/00* (2018.01)
*A01H 6/00* (2018.01)
*A01H 5/02* (2018.01)

(52) U.S. Cl.
USPC ..... Plt./252
CPC ..... *A01H 6/00* (2018.05); *A01H 5/02* (2013.01)

(58) Field of Classification Search
USPC ..... Plt./252
CPC ..... A01H 5/00
See application file for complete search history.

(56) References Cited

U.S. PATENT DOCUMENTS

PP27,194 P3 * 9/2016 Helvick et al. ..... A01H 5/00 Plt./252

* cited by examiner

*Primary Examiner* — Annette H Para
(74) *Attorney, Agent, or Firm* — Klarquist Sparkman, LLP

(57) ABSTRACT

A new crapemyrtle plant has deep, uniform purple foliage and stems; a true pink flower color; an intermediate upright growth habit; and powdery mildew and Cercospera resistance.

2 Drawing Sheets

Latin name of the genus and species of the plant claimed: 'DJ 01-14' is a Crapemyrtle plant that is a *Lagerstroemia* hybrid.

Variety denomination: The new crapemyrtle plant claimed is a variety denominated 'DJ 01-14'.

BACKGROUND OF THE INVENTION

The present invention relates to the discovery of a new and distinct cultivar of the ornamental flowering shrub *Lagerstroemia indica* x *Lagerstroemia fauriei*, commonly known as crapemyrtle, and hereafter referred to by the varietal denomination 'DJ 01-14', as herein described and illustrated.

The new crapemyrtle originated from open pollinated seed of a patented plant, 'Chocolate Mocha' Crapemyrtle (U.S. Plant Pat. No. 21,450). 'DJ 01-14' was selected from plants grown at a Horticulture Farm in Watkinsville, Ga. The seedlings were planted in containers and selections were made for plants based on the following criteria:

1.) Intermediate, upright (normal) growth habit
2.) Powdery mildew resistance
3.) Flower color and quality
4.) Deep purple foliage and stem color 'DJ 01-14' was selected in September 2014.

Asexual reproduction by traditional vegetative cuttings since 2014 at the Horticulture Farm in Watkinsville, Ga. has shown that the distinguishing characteristics of the new crapemyrtle variety, 'DJ 01-14' are stable and reproduced true to type in successive generations.

SUMMARY OF THE INVENTION

'DJ 01-14' has not been observed under all possible environmental conditions. The phenotype may vary somewhat with changes in light, temperature, soil and rainfall amount, however, any variance in genotype.

The following traits have been observed and represent the characteristics of the new cultivar. Asexual propagation by cuttings has proven that these characteristics are firmly fixed in succeeding asexually propagated generations. In combination, these characteristics distinguish 'DJ 01-14' from all other varieties known to the inventor:

1.) Deep, uniform, purple foliage and stems;
2.) True pink flower color;
3.) Intermediate, upright growth habit; and
4.) Powdery mildew and Cercospera resistance.

'DJ 01-14' is distinguished from its parent plant *Lagerstroemia indica* x *Lagerstroemia fauriei* 'Chocolate Mocha' by its improved, more consistent, deeper purple foliage and its larger, truer pink flowers. 'DJ 01-14' over 3 years of evaluation, has proven to be more resistant to powdery mildew and Cercospera than 'Chocolate Mocha'.

DESCRIPTION OF THE DRAWINGS

The accompanying colored photographic illustration shows the overall appearance and distinct characteristics of the new 'DJ 01-14' cultivar. The colors in the photograph are as close as possible with the photographic and printing technology utilized.

DETAILED DESCRIPTION

Figure 1:
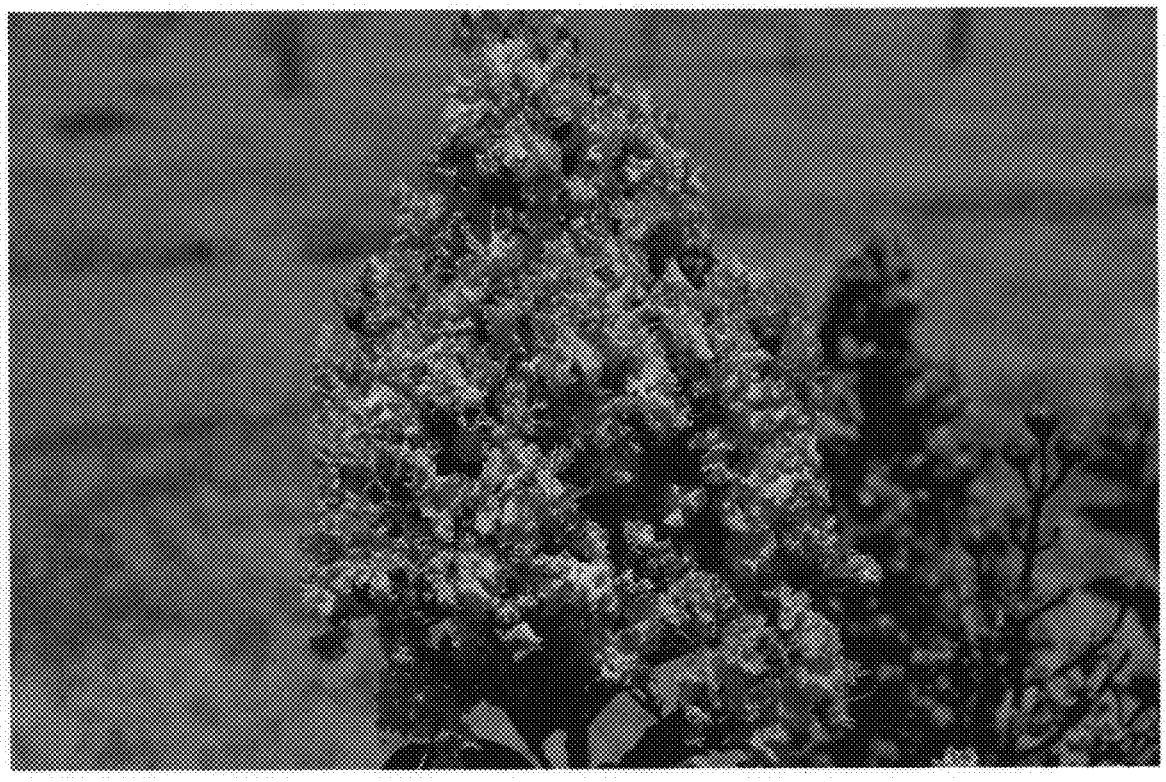
FIG. 1 is a close up view of the flowers of the 'DJ 01-14' variety.
Figure 2:
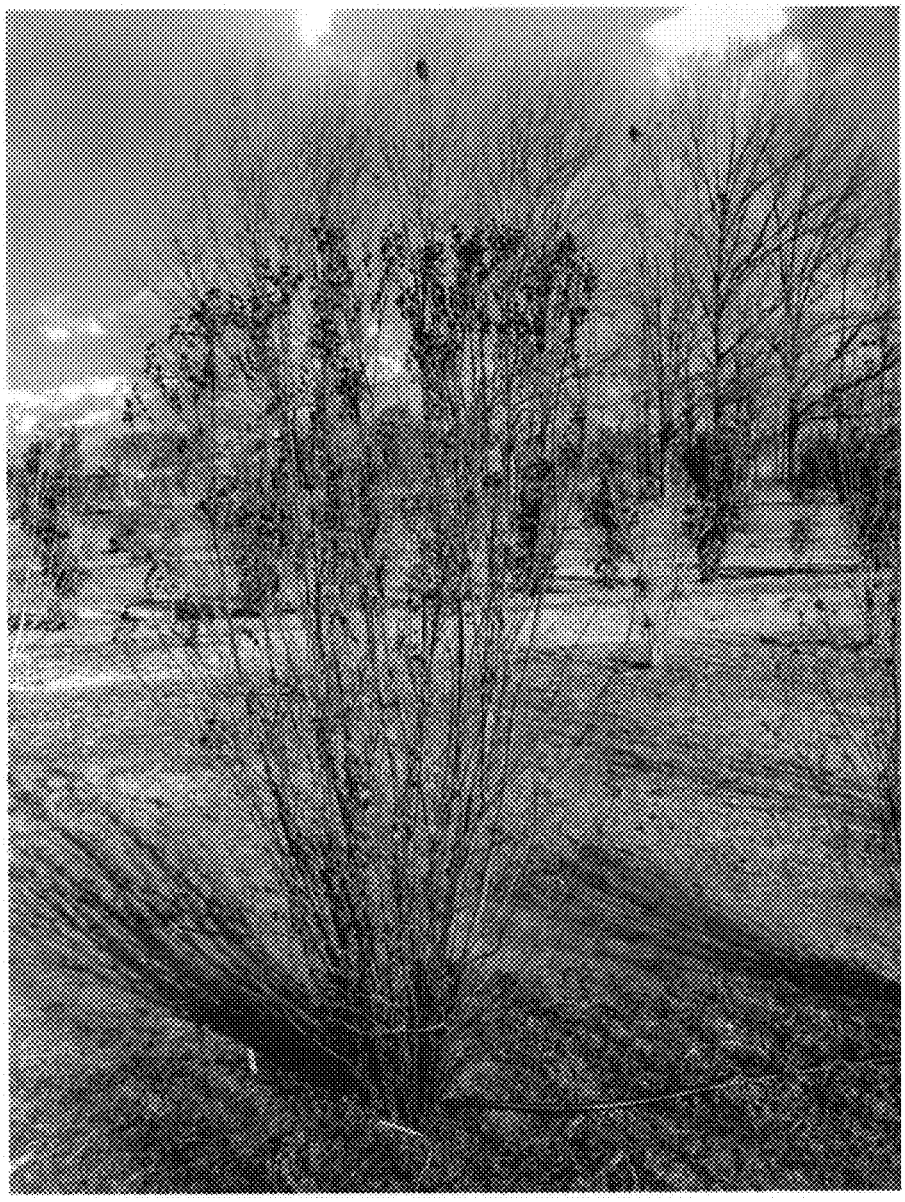
FIG. 2 is a view of an entire five year old plant of the 'DJ 01-14' variety.

In the following description, color references are made to The Royal Horticulture Society Colour Chart, 2015 Edition, except where general terms of ordinary dictionary significance are used. Plants used for the description were approximately 2.5 years old and grown in 11.4 liter containers in full sun at a Horticulture Farm in Watkinsville, Ga.

'DJ 01-14' is a cultivar of *Lagerstroemia indica* x *Lagerstroemia fauriei* 'Chocolate Mocha'. The current variety is a progeny from seed collected from 'Chocolate Mocha' in November of 2013. The male, or pollen parent is unknown (open-pollinated).

Propagation: Vegetatively by softwood stem cuttings. Softwood stem cuttings root readily at 20-25° C.

General description: Flowering shrub; compact, upright, intermediate growth habit. Freely branching; lateral branches abundant without pruning (although some winter pruning of dead wood is recommended). Ultimately, proper pruning will result in a fine-textured, dense habit.

Root description: Numerous, fine, fibrous and well branched, color 155D. Young roots are fibrous, and old roots are woody.

Root development: Average of 6 weeks at 25 degrees C. for root initiation and average of 3 months at 30 degrees C. to produced young rooted plant.

Plant size: The original plant at 3.5 years is 152 cm high from the soil level to the top of the uppermost inflorescences and about 91 cm wide.

Blooming period: June through September in Watkinsville, Ga. Rebloom after 6-8 weeks when spent flowers are removed.

Plant type: Deciduous flowering shrub.

Plant habit: Compact, branching, upright in outline, finely textured, freely branched without pruning.

Height and spread: Average of 2.4 meters in height and 1 meter in width.

Cold hardiness: USDA zones 6-8.

Diseases: Resistant to powdery mildew and cercospera leaf spot.

Growth rate: Moderate.

Branch despription:

- *Branch shape*.—Tetragonal on first year growth; round on second year growth.
- *Branch color*.—First year; N79B, second year 199C, trunk 199B.
- *Branch size*.—Main branch: First year 30 cm in length and 6 mm in diameter, Second year: 65 cm in length and 10 mm in diameter, lateral branches are 70-75 cm in length and 2 cm in diameter, Trunk; multi-branched and 2.75 cm in diameter at soil level.
- *Branch surface*.—Lateral branches sparsely covered with irregular lenticels 177B in color, trunk fine, smooth barked, young bark 177B, older bark 199C.
- *Branch strength*.—Young; flexible but strong, mature; easily snapped.
- *Branching*.—Freely branching habit without pruning, average of 8 lateral branches.
- *Branch aspect*.—Held at angles between 30-60 degrees. Internode length average of 3 cm.
- *Vegetative buds*.—Alternate sub-opposite in arrangement, avg. of 4 mm in length 3 mm in width, conical in shape, 5-scaled imbricate and lack pubescence, color N79B.

Foliage description:

- *Leaf shape*.—Elliptic, leaf division is single (simple).
- *Leaf base*.—Cuneate, smooth.
- *Leaf apex*.—Acute to abruptly acuminate, smooth.
- *Leaf veination*.—Pinnate, upper surface N187A, lower surface N187D.
- *Leaf margins*.—Entire.
- *Leaf arrangement*.—Sub-opposite to alternate.
- *Leaf attachment*.—Petiolate.
- *Leaf surface*.—Upper surface glossy, glabrous, waxy; lower surface dull, slightly pubescent.
- *Leaf size*.—Average 3.5 cm in length and average 2 cm in width.
- *Leaf quantity*.—Average of 70 per lateral branch.
- *Leaf color*.—Young upper surface; N185A, young lower surface N186A; mature upper surface; N186A, mature lower surface N187B.
- *Petiole*.—Average 1 mm in length and 1 mm in diameter, surface texture smooth, glabrous, N186B moderate-strong.

Flower description:

- *Inflorescence type*.—Terminal panicle; 15 thryses, thryses pyramidal conical, 5 mm long.
- *Persistence of inflorescence*.—Inflorescences are showy for an average of 4 weeks, individual flowers persist for an average of 2 days, self cleaning.
- *Inflorescence size*.—An average of 20 cm in height and 15 cm in width.
- *Inflorescence number*.—Terminally born, 1 per lateral branch.
- *Flower number*.—Average of 8 flowers and flower buds per inflorescence.
- *Flower fragrance*.—Light sweet scent.
- *Flower buds*.—Obovate in shape, and average of 5 mm in length, 9 mm wide, rounded apex, surface is lustrous with 6 distinct suture lines, color is 183B.
- *Flower aspect*.—Upright to outward.
- *Flower type*.—Actinomorphic.
- *Flower size*.—Average of 1.2 cm in diameter.
- *Petals*.—Typically 6. Rotate/whorled in arrangement, fan shaped, ruffled margins, sagittate base, ruffled and rounded apex. Both surfaces glabrous, and average of 5 mm in length and 10 mm wide. Color when opening, and when fully opened upper and lower surface; N66D.
- *Calyx*.—Consists of 6 sepals fused at base acute apices and average of 7 mm in length and 10 mm in width, 183 B in color on both surfaces, smooth and glabrous on both surfaces, narrowly triangular in shape, apex is acuminate, margin is entire, fine texture.
- *Peduncles*.—Strong, average 7 cm in length and 3 mm in diameter. N186C in color. Surface is covered with fine appressed pubescences, strong.
- *Pedicels*.—Strong, average of 8 mm in length and 1 mm in diameter N186C in color. Surface is covered with fine appressed pubescences.

Reproductive organs:

*Stamens*.—25-30 stamens clustered in the center. 6 mm in length surrounded by 6 longer stamens, 1 cm in length, glabrous, surface, anthers; 12A in color, pollen color is 12A.

*Pistils*.—Single(1), average of 2 cm in length and width; style is 1.5 cm in length and 59D in color; stigma, rounded less than 1 mm in diameter, 59D in color; ovary, superior, 157C in color, 3 mm in diameter.

Fruit and seed: Capsule; 6 valved dehiscent, broad rounded in shape 8 mm in length and diameter, immature seed color is 141C and mature color is N199, each capsule contains 25 seeds, average of 6 mm in length and 3 mm in width and N199B in color; Fruit: oval, rounded, fruit depression at the apex absent; fruit depression at base absent.

*Pest resistance*.—Neither resistance to nor susceptibility to normal pests of *Lagerstroemia* plants has been observed.

We claim:

1. A new and distinct cultivar of the Crapemyrtle plant named 'DJ 01-14', as herein illustrated and described.

* * * * *